(12) United States Patent
Quinn et al.

(10) Patent No.: US 10,406,296 B2
(45) Date of Patent: *Sep. 10, 2019

(54) TELESCOPING SAFETY SHIELD FOR NEEDLES

(71) Applicant: Becton, Dickinson and Company, Franklin Lakes, NJ (US)

(72) Inventors: Michael Vincent Quinn, East Hanover, NJ (US); Mark DiSilvestro, Westwood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/667,158

(22) Filed: Aug. 2, 2017

(65) Prior Publication Data

US 2017/0326310 A1 Nov. 16, 2017

Related U.S. Application Data

(60) Continuation of application No. 14/596,736, filed on Jan. 14, 2015, now Pat. No. 9,750,894, which is a division of application No. 12/490,578, filed on Jun. 24, 2009, now Pat. No. 9,352,102.

(60) Provisional application No. 61/075,104, filed on Jun. 24, 2008.

(51) Int. Cl.
*A61M 5/32* (2006.01)

(52) U.S. Cl.
CPC ........ *A61M 5/3243* (2013.01); *A61M 5/3202* (2013.01); *A61M 5/3245* (2013.01); *A61M 5/3257* (2013.01); *A61M 5/3271* (2013.01); *A61M 5/3275* (2013.01); *A61M 2005/3247* (2013.01); *A61M 2005/3267* (2013.01)

(58) Field of Classification Search
CPC .............. A61M 5/3243; A61M 5/3202; A61M 5/3245; A61M 5/3257; A61M 5/3271; A61M 5/3275

See application file for complete search history.

(56) References Cited

U.S. PATENT DOCUMENTS

| | | |
|---|---|---|
| 2,740,404 A | 4/1956 | Kohl |
| 4,425,120 A | 1/1984 | Sampson et al. |
| 4,500,310 A | 2/1985 | Christinger |
| 4,573,976 A | 3/1986 | Sampson et al. |

(Continued)

OTHER PUBLICATIONS

BD Safety-Lock Sliding Sleeve Syringe, BD Medical Systems, 1999.

*Primary Examiner* — Edelmira Bosques
(74) *Attorney, Agent, or Firm* — The Webb Law Firm

(57) ABSTRACT

A safety shield adapted for use with a syringe having a syringe barrel for protecting a needle after use in a medical procedure is disclosed. The safety shield includes a first portion disposed at least partially about the barrel and axially movable from a retracted position surrounding at least a portion of the syringe barrel to an extended position wherein at least the distal end of the first portion extends beyond the distal end of the syringe barrel. The shield further includes a second portion associated with the first portion and axially movable with respect to the first portion from a retracted position to an extended position extending beyond the distal end of the first portion. First and second locking members are provided for locking the first and second portions in an extended position upon axial movement thereof.

8 Claims, 11 Drawing Sheets

(56) References Cited

U.S. PATENT DOCUMENTS

| | | |
|---|---|---|
| 4,631,057 A | 12/1986 | Mitchell |
| 4,731,059 A | 3/1988 | Wanderer et al. |
| 4,747,837 A | 5/1988 | Hauck |
| 4,804,372 A | 2/1989 | Laico et al. |
| 4,894,055 A | 1/1990 | Sudnak |
| 4,897,083 A | 1/1990 | Martell |
| 4,923,447 A | 5/1990 | Morgan |
| 4,931,043 A | 6/1990 | Ray et al. |
| 4,973,308 A | 11/1990 | Borras et al. |
| 4,998,924 A | 3/1991 | Ranford |
| 5,002,533 A | 3/1991 | Jullien |
| 5,019,051 A | 5/1991 | Hake |
| 5,057,087 A | 10/1991 | Harmon |
| 5,304,149 A | 4/1994 | Morigi |
| 5,312,370 A | 5/1994 | Talonn et al. |
| 5,336,199 A | 8/1994 | Castillo et al. |
| 5,338,310 A | 8/1994 | Lewandowski |
| 5,342,309 A | 8/1994 | Hausser |
| 5,385,555 A | 1/1995 | Hausser |
| 5,397,313 A | 3/1995 | Gross |
| 5,411,488 A | 5/1995 | Pagay et al. |
| 5,411,489 A | 5/1995 | Pagay et al. |
| 5,439,450 A | 8/1995 | Haedt |
| 5,611,782 A | 3/1997 | Haedt |
| 5,647,849 A | 7/1997 | Kalin |
| 5,658,254 A | 8/1997 | Reichenbach et al. |
| 5,674,203 A | 10/1997 | Lewandowski |
| 5,688,252 A | 11/1997 | Matsuda et al. |
| 5,733,264 A | 3/1998 | Flowers |
| 5,772,636 A | 6/1998 | Brimhall et al. |
| 5,919,172 A | 7/1999 | Golba, Jr. |
| 5,928,202 A | 7/1999 | Linnebjerg |
| 5,947,933 A | 9/1999 | Reichenbach et al. |
| 6,080,135 A | 6/2000 | Van Stokkum |
| 6,129,712 A | 10/2000 | Sudo et al. |
| 6,514,229 B1 | 2/2003 | Huang et al. |
| 6,749,590 B2 | 6/2004 | Niedospial, Jr. |
| 6,869,415 B2 | 3/2005 | Asbaghi |
| 6,991,618 B2 | 1/2006 | Lau et al. |
| 7,147,624 B2 | 12/2006 | Hirsiger et al. |
| 7,166,089 B2 | 1/2007 | Huang |
| 9,352,102 B1 * | 5/2016 | Quinn ................ A61M 5/3271 |
| 9,750,894 B2 * | 9/2017 | Quinn ................ A61M 5/3271 |
| 2007/0088270 A1 | 4/2007 | Cude |
| 2008/0021409 A1 * | 1/2008 | Pessin ................ A61M 5/3257 604/198 |

\* cited by examiner

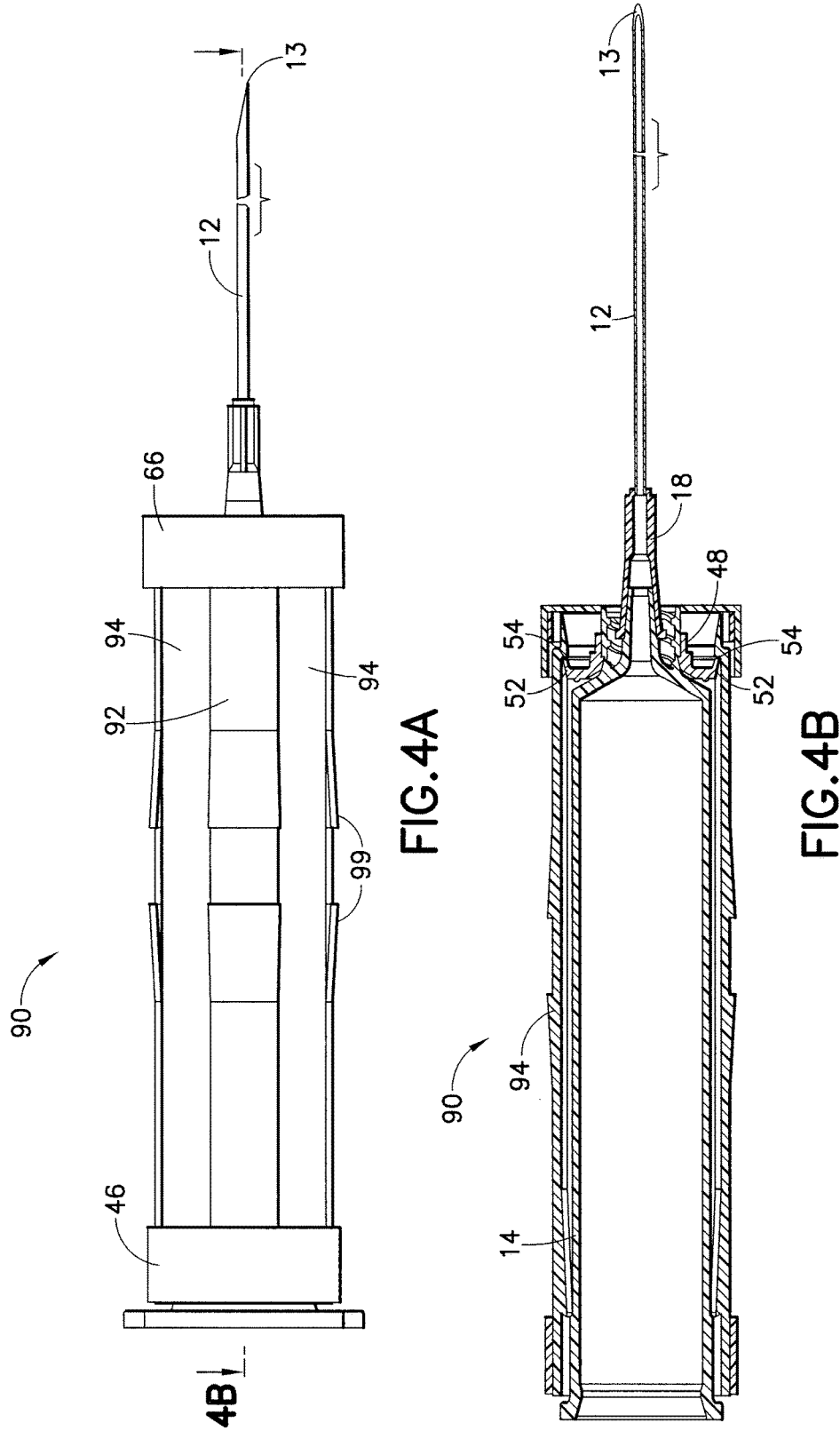

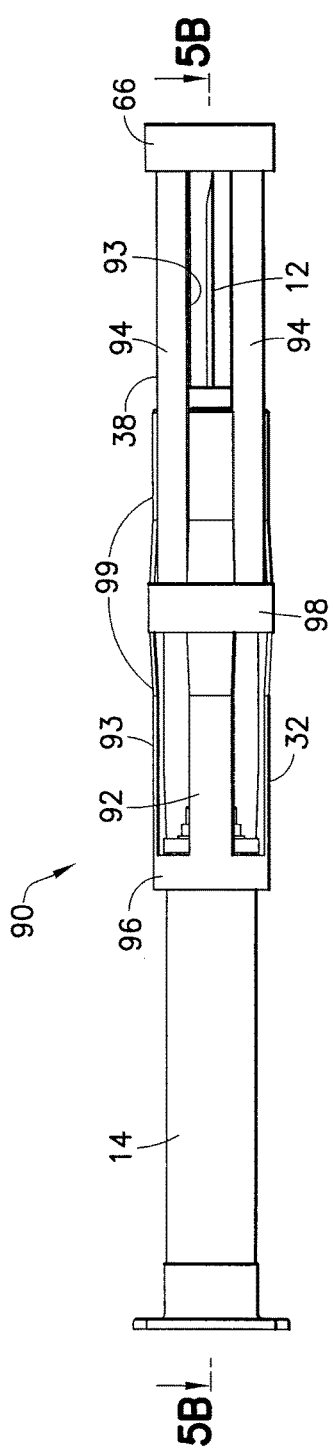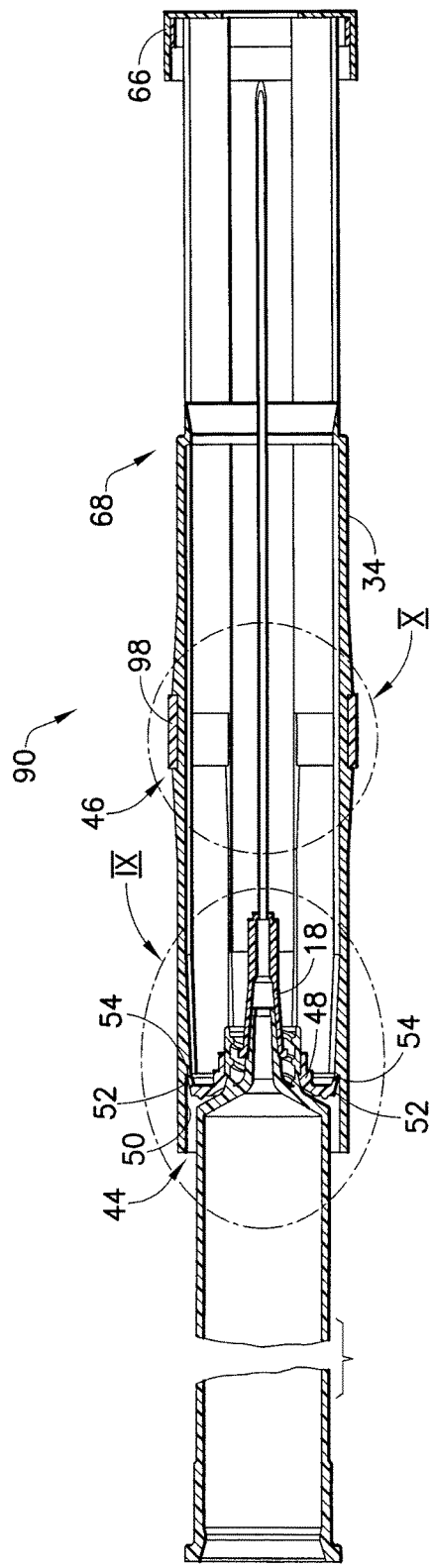

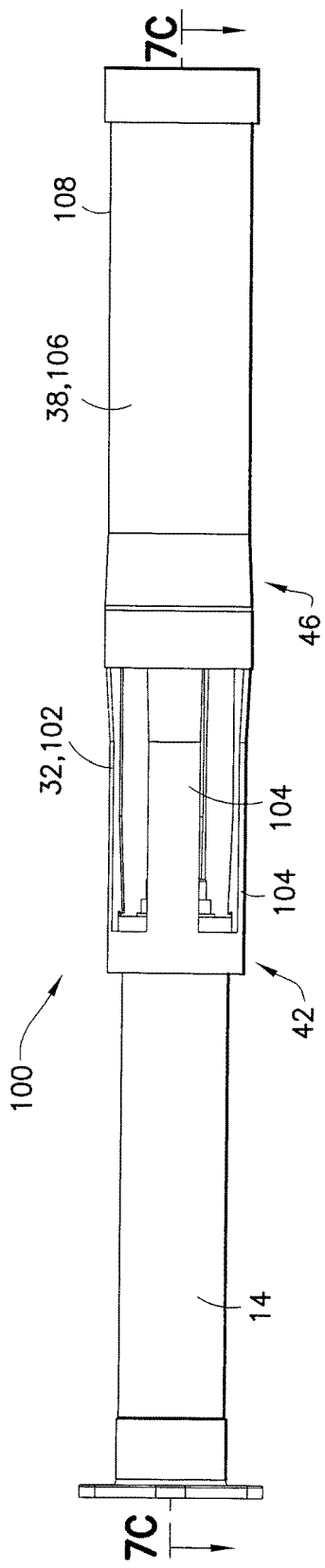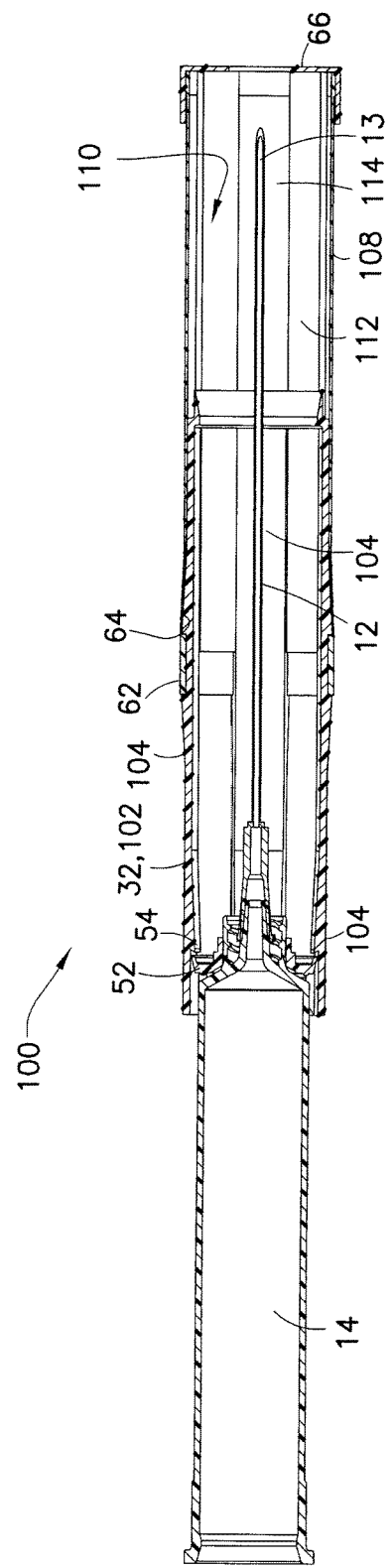

TELESCOPING SAFETY SHIELD FOR NEEDLES

CROSS REFERENCE TO RELATED APPLICATIONS

This application is a continuation of U.S. patent application Ser. No. 14/596,736, filed Jan. 14, 2015, which is a divisional of U.S. patent application Ser. No. 12/490,578 filed Jun. 24, 2009, now U.S. Pat. No. 9,352,102, which claims priority to U.S. Provisional Application No. 61/075,104 filed Jun. 24, 2008, the entire contents of each of which are herein incorporated by reference.

BACKGROUND OF THE INVENTION

Field of the Invention

The invention relates, in general, to a safety shield adapted for use with a syringe for protecting a needle after use in a medical procedure and, more particularly, to a safety shield adapted for extending to nearly twice the length of a syringe barrel to protect an extended length needle.

Description of Related Art

There is an ever-increasing need for the use of syringes having longer needles for completing specific medical procedures. The use of these longer needles is often necessary to ensure proper medication delivery. Along with the use of longer needles, a need has arisen for ways in which to properly shield these longer needles to prevent accidental needle sticks after completion of the procedure.

Shields for protecting needles after use in medical procedures are known. Such devices protect medical personnel from needle sticks after such needles have been used in a medical procedure. Different types of shields currently on the market include hinged shields which rotate 90-180 degrees to cover the needle, and spring activated shields which are actively or passively activated to extend through a needle hub to cover the needle. These designs are not concerned with long needle safety and may be too cumbersome to convert to use with a longer needle.

An example of a device for shielding a needle is shown in U.S. Pat. No. 6,869,415 to Asbaghi. This device includes a guard member that is restrained in a proximal position within a guide way. When a blood collection vial is engaged with the device, the guard member is automatically released to move distally over the needle as the needle is being withdrawn from the patient.

Another example of a shielding device currently in use is the SAFETY-LOK™ device available from Becton, Dickinson and Company, the Assignee of the current invention. In the SAFETY-LOK™ device, a cylindrical shield with an end cap is positioned around the barrel of a standard syringe. After the syringe is used for an injection, the shield is advanced forward by the user until it extends fully over the end of the needle and locks into place via a collar that is press-fit around the luer threads. U.S. Pat. No. 4,631,057 to Mitchell also shows a cylindrical shield which is positioned about the barrel of a syringe, which can be advanced forward after use of the needle. These existing devices are limited with respect to the length of a needle that can be protected because the shield can only be as long as the barrel of the syringe. Additionally, viewing of the graduated markings on the syringe barrel and/or the contents of the syringe barrel can be impaired due to the thickness and/or clarity of the shield when in the retracted position surrounding the barrel.

U.S. Pat. Nos. 7,147,624; 6,514,229; 6,080,135; 5,772,636; 5,336,199; 4,897,083; and 4,804,372 all show needle sheaths including multiple nested members mounted to a needle base. Upon the completion of a medical procedure, these nested members are expanded in a forward direction to cover the needle and protect the user from unwanted needle sticks. These devices are limited in needle length which can be covered because the nested devices can only have a certain thickness. Otherwise, the syringe can become difficult to handle.

SUMMARY OF THE INVENTION

There is a need in the art for a needle shield capable of expanding to a length sufficient for covering a needle and protecting against needle sticks wherein the needle has an extended length, i.e., needles having a length which is substantially equal to or longer than a length of a syringe barrel to which the needle is attached. There is a further need in the art to produce needle shields which are relatively inexpensive to manufacture and do not hinder the user's handling of the syringe. There is a further need in the art for a needle shield which has a reduced thickness so that the handling of the syringe during use is not affected. There is still a further need in the art for a needle shield which enables easy viewing of the graduating markings on the syringe barrel and/or viewing of the contents contained within the syringe.

According to one embodiment, the invention is directed to a shieldable syringe including a syringe barrel extending between a proximal end and a distal end and defining a chamber therein. A safety shield is attached to the syringe barrel. The shield includes a first portion having a proximal end and a distal end. The first portion is disposed at least partially about the barrel and axially movable from a retracted position surrounding at least a portion of the syringe barrel to an extended position wherein at least the distal end of the first portion extends beyond the distal end of the syringe barrel. A second portion is associated with the first portion. The second portion has a proximal end and a distal end and is axially movable with respect to the first portion from a retracted portion to an extended position extending beyond the distal end of the first portion. A first locking member is provided for restraining and/or locking the proximal end of the first portion with respect to the distal end of the barrel upon axial movement of the first portion to the extended position. A second locking member is provided for restraining and/or locking the proximal end of the second portion with respect to a distal end of the first portion upon axial movement of the second portion to the extended position.

The syringe barrel may define a barrel length between the proximal end and the distal end, and may be adapted at the distal end thereof for use with a needle cannula. The safety shield may also be adapted for shielding needles having a length which is substantially equal to or longer than the barrel length. The retracted position of the first portion may include a non-shielding position surrounding at least a portion of the syringe barrel, and the extended position of the first portion may include a telescoped shielding portion adapted for encompassing at least a portion of the needle cannula extending from the distal end of the syringe barrel. The retracted position of the second portion may include a non-shielding position surrounding at least a portion of the first portion, and the extended position of the second portion may include a telescoped shielding position wherein the distal end of the second portion is adapted for encompassing a distal tip of the needle cannula. Optionally, the first and second portions may be adapted to axially move as a single unit until the first locking member locks the proximal end of the first portion to a distal end of the syringe barrel.

The syringe barrel may include a locking collar proximate the distal end thereof for lockingly engaging an inner surface of the first locking member upon axial movement of the first portion to the extended position. The locking collar may further include at least one detent and the inner surface of the first locking member includes at least one barb extending radially inward for engaging the at least one detent to lock the first portion in the extended position. The at least one barb can include a series of bilaterally opposing barbs which lock onto at least one circumferentially extending detent on the locking collar. The second locking member may include at least one locking barb extending at least partially about a circumference of an outer surface of the distal end of the first portion and at least one locking ledge radially extending from an inner surface of the proximal end of the second portion for lockingly engaging the locking ledge upon axial movement of the second portion from the retracted position to the extended position. The at least one locking barb extending at least partially about a circumference of an outer surface of the distal end of the first portion preferably includes a first locking barb and a second locking barb positioned a predetermined distance along the length of the distal end of the first portion to create a circumferential channel. The channel may be adapted for receiving the locking ledge radially extending from the inner surface of the proximal end of the second portion upon movement of the second portion to the extended position. The locking ledge may also extend substantially continuously about the inner circumference of the proximal end of the second portion, and the first locking barb and the second locking barb may be axially spaced about the outer circumference of the distal end of the first portion. This locking ledge includes a rearward stop, and a forward stop wherein the rearward stop is adapted for cooperating with the first locking barb to prevent the second portion from retracting with respect to the first portion upon expansion of the shield. The forward stop may be adapted for cooperating with the second locking barb to prevent the second portion from extending beyond the second locking member upon expansion of the shield to the extended position. Further, the distal end of the second portion may include a shield cap for encompassing a distal tip of the needle cannula.

In one configuration, the first portion may include an inner portion having a first diameter and a second portion including an outer portion having a second diameter wherein the second diameter is greater than the first diameter for enclosing at least a portion of the inner portion. The outer portion may be adapted for telescoping movement with respect to the inner portion.

In another configuration, the first portion may include a first series of longitudinally extending, axially-spaced slats arranged circumferentially defining a first diameter which may be adapted for axial movement from the retracted position to the extended position, and the second portion may include a second series of longitudinally extending axially-spaced slats arranged between the first series of slats in the retracted position. The second series of slats may be adapted for axial movement from the retracted position to the extended position with respect to the first series of slats. The first locking member may be adapted for locking the proximal end of the first portion to the distal end of the syringe barrel upon axial movement of the first series of the slats from the retracted position to the extended position and the second locking member may be adapted for locking the proximal end of the second portion to the distal end of the first portion upon axial movement of the second series of slats from the retracted position to the extended position wherein the distal end of the second portion may be adapted for enclosing at least a portion of a distal tip of the needle cannula after use of the syringe. The first portion may include a first holding ring for securing the first series of slats thereto and the second portion includes a second holding ring for securing the second series of slats.

The first and second holding rings may be associated with one another to cause the first series of slats to be held in interengaging contact with the second series of slats. Axial movement of the second holding ring with respect to the first holding ring may cause the first and second series of slats to become separated from one another to achieve expansion of the shield. Shield-to-shield locks may also be provided for holding the first portion and the second portion in interengaging contact with one another at least partially about the barrel during use of the syringe. The shield-to-shield locks may include interlocking members positioned along edge portions of the first and second series of slats.

In yet another configuration, the first portion may include an inner portion having a first diameter defined by a first series of axially-spaced circumferentially arranged slats, and the second portion may include an outer portion having a second diameter which is greater than the first diameter for enclosing at least a portion of the inner portion. The outer portion may be adapted for telescoping movement with respect to the inner portion. The outer portion has a continuous outer surface and an inner surface comprising a second series of axially-spaced circumferentially arranged slats connected by a series of axially-spaced circumferentially spaced connecting portions. The axially-spaced connecting portions are adapted for mating engagement with the first series of axially-spaced slats when the first and second portions are disposed at least partially about the barrel.

According to another embodiment, the invention is directed to a safety shield which may be adapted for use in connection with, and attachable to, a syringe barrel. The safety shield includes a first portion adapted for concentrically mounting about the syringe barrel and adapted for telescoping movement with respect to the syringe barrel, and a second portion mounted with respect to the first portion. The first portion and the second portion are mounted for axial movement from a retracted position at least partially surrounding the syringe barrel to an extended position. The extended positions of the first and second portions define an extended length that is approximately twice the length of the syringe barrel.

The safety shield includes at least one locking member for locking the first and second portions in the extended position. The at least one locking member may include a first locking member adapted for locking a proximal end of the first portion to a distal end of the syringe barrel, and a second locking member adapted for locking a proximal end of the second portion to a distal end of the first portion.

In one configuration, the first portion may include an inner portion having a first diameter, and the second portion may include an outer portion having a second diameter wherein the second diameter is greater than the first diameter for enclosing at least a portion of the inner portion. The outer portion may be adapted for telescoping movement with respect to the inner portion.

In another configuration, the first portion may include a first series of longitudinally extending, axially-spaced slats arranged circumferentially defining a first diameter, which may be adapted for axial movement from the retracted position to the extended position, and the second portion may include a second series of longitudinally extending axially-spaced slats arranged between the first series of slats in the retracted position. The second series of slats may be adapted for axial movement from the retracted position to the extended position with respect to the first series of slats.

In yet another configuration, the first portion may include an inner portion having a first diameter defined by a first series of axially-spaced circumferentially arranged slats, and the second portion may include an outer portion having a second diameter which is greater than the first diameter for enclosing at least a portion of the inner portion. The outer portion may be adapted for telescoping movement with respect to the inner portion. The outer portion has a continuous outer surface and an inner surface including a second series of axially-spaced circumferentially arranged slats connected by a series of axially-spaced connecting portions. The axially-spaced connecting portions are adapted for mating engagement with the first series of axially-spaced slats when the first and second portions are disposed at least partially about the barrel.

In accordance with yet another embodiment, the invention is directed to a method for shielding a needle cannula of a syringe. The syringe may include a syringe barrel extending between a proximal end and a distal end, defining a chamber therein. The method may include the steps of providing a safety shield having a first portion and a second portion. The first portion of the safety shield may have a proximal end and a distal end. The first portion may be disposed at least partially about the barrel and may be axially movable from a retracted position, surrounding at least a portion of the barrel, to an extended position, extending beyond the distal end of the syringe barrel. The method further includes the step of providing a second portion associated with the first portion. The second portion may have a proximal end and a distal end, and may be axially movable with respect to the first portion from a retracted position, to an extended position extending beyond the distal end of the first portion. The method further includes the step of providing a first locking member for locking the proximal end of the first portion with respect to a distal end of the barrel upon axial movement of the first portion from the retracted position to the extended position. The method further includes the step of providing a second locking member for locking the proximal end of the second portion with respect to the distal end of the first portion upon axial movement of the second portion from the retracted position to the extended position. The method may also include the steps of axially moving the first portion from the retracted position to the extended position, and axially moving the second portion from the retracted position to the extended position to cause the second portion to surround at least a portion of a distal tip of the extended length needle cannula.

The syringe barrel may define a barrel length between the proximal end and the distal end and may be adapted at the distal end thereof for use with a needle cannula having a length substantially equal to or longer than the barrel length. In one configuration, the moving steps cause the first and second portions to axially move as a single unit until the first locking member locks the proximal end of the first portion to the distal end of the barrel, and the second portion continues to be extended in the forward direction until the distal end of the second portion encompasses at least a portion of the distal end of the needle cannula. The method may further include the step of providing a shield cap at the distal end of the second portion for encompassing the distal tip of the needle after use.

In accordance with yet another embodiment, the invention is directed to a shieldable syringe comprising a syringe barrel extending between a proximal end and a distal end and defining a chamber therein. The syringe includes a safety shield attached to the syringe barrel. The safety shield includes a first portion having a proximal end, a distal end, and a length which is less than or equal to a length of the syringe barrel. This first portion is disposed at least partially about the barrel. The safety shield further includes a second portion having a proximal end, a distal end, and a length which is less than or equal to the length of the first portion and the syringe barrel. The second portion is associated with the first portion, and the first and second portions are mounted for axial movement from a retracted position at least partially surrounding the syringe barrel to an extended position defining an extended length which is approximately less than or equal to twice the length of the syringe barrel. The syringe barrel defines a barrel length between the proximal end and the distal end and may be adapted at the distal end thereof for use with a needle cannula having a length substantially equal to or longer than the barrel length. According to an embodiment, the lengths of the first portion and the second portion may be approximately equal to the length of the syringe barrel and the extended length may be approximately equal to twice the length of the syringe barrel.

As stated above, the present invention provides for three separate embodiments of the safety shield as discussed briefly below.

According to a first configuration of the inventive safety shield, the first portion includes an inner portion having a first diameter and a second portion comprises an outer portion having a second diameter. The second diameter is greater than the first diameter so that the outer portion encloses at least a portion of the inner portion. The outer portion includes a distal end and a proximal end and is adapted for telescoping movement with respect to the inner portion.

According to a second configuration of the safety shield, the first portion includes a first series of longitudinally extending, axially-spaced slats arranged circumferentially defining a first diameter for enclosing at least a portion of a syringe barrel. The first portion is adapted for axial movement from a retracted to an extended position with respect to the syringe barrel. The second portion includes a second series of longitudinally extending, axially-spaced slats arranged between the first series of slats when the shield is in the retracted position. The second series of slats have a second diameter, which is substantially equal to the first diameter for enclosing at least a portion of the syringe barrel. The second portion is adapted for axial movement from a retracted to an extended position with respect to the first series of slats. The first locking member is adapted for locking the proximal end of the first portion to the distal end of the syringe barrel upon axial movement of the first series of the slats from the retracted position to the extended position, and the second locking member is adapted for locking the proximal end of the second portion to the distal end of the first portion upon axial movement of the second series of slats from the retracted position to the extended position wherein the distal end of the second portion is adapted for enclosing at least a portion of a distal tip of the needle cannula after use of the syringe. The first portion includes a first holding ring for securing the first series of slats thereto, and the second portion includes a second holding ring for securing the second series of slats. The first and second holding rings are associated with one another to cause the first series of slats to be held in interengaging contact with the second series of slats. Axial movement of the second holding ring with respect to the first holding ring causes the first and second series of slats to become separated from one another to achieve expansion of the shield. Shield-to-shield locks are provided for holding the first portion and the second portion in interengaging contact with one another at least partially about the barrel during use of the syringe. These shield-to-shield locks can be interlocking members positioned along edge portions of the first and second series of slats.

According to a third configuration of the safety shield, the first portion includes an inner portion having a first diameter. The inner portion includes a first series of axially-spaced slats arranged circumferentially defining a first diameter for enclosing at least a portion of the syringe barrel. The second portion includes an outer portion having a second diameter that is greater than the first diameter. The outer portion has a continuous outer surface. The inner surface of this outer portion includes a second series of axially-spaced circumferential slats connected by a series of axially-spaced circumferential connecting portions which have a thickness that is complementary to the first series of slats. These connecting portions are adapted for mating engagement with this first series of slats when the shield is in a retracted or non-shielding position. Upon expansion or axial movement of the sheath to an extended or shielding position, the second or outer portion continuously surrounds a distal portion of the needle.

BRIEF DESCRIPTION OF THE DRAWINGS

FIG. 4A is a side view of a syringe similarly configured to the syringe shown in FIG. 1 including the safety shield according to a second embodiment of the invention in a retracted position;

FIG. 4B is a cross-sectional side view taken along line 4B-4B of the syringe of FIG. 4A;

FIG. 5A is a side view of the syringe of FIG. 4A in the extended position;

FIG. 5B is a cross-sectional side view taken along line 5B-5B of FIG. 5A;

FIG. 7B is a side perspective view of the syringe of FIG. 7A in the expanded position;

FIG. 7C is a cross-sectional side view of the syringe taken along line 7C-7C of FIG. 7B;

DETAILED DESCRIPTION OF THE INVENTION

Figure 1:
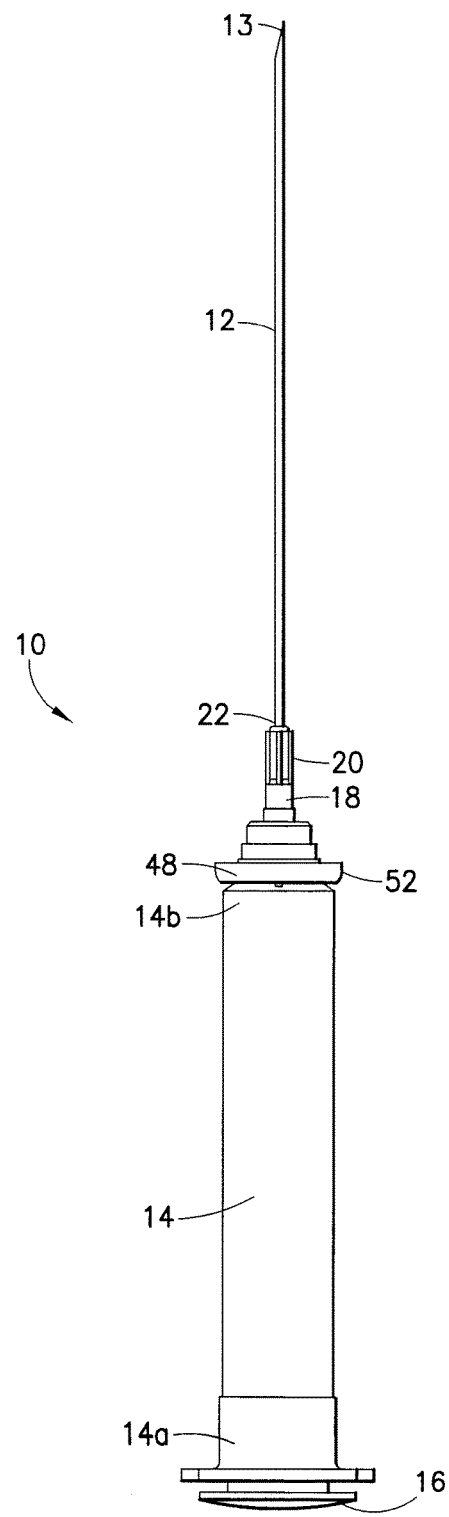
FIG. 1 is a side view of a syringe having an extended length needle and a safety sheath in accordance with a first embodiment of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIG. 1, which shows a syringe, generally indicated as 10, having an extended length needle cannula 12, which may be safety shielded to protect the needle cannula 12 and its tip 13 after use in a medical procedure. In one embodiment, the needle cannula 12 can have an extended length of up to about five inches. The syringe 10 includes a syringe barrel 14, a plunger rod 16 adapted for movement within the syringe barrel 14, a luer 18 secured to the syringe barrel 14, and a needle hub 20 secured to the luer 18. The syringe barrel 14 extends between a proximal end 14a and a distal end 14b and defines a chamber therein. The syringe barrel 14 defines a barrel length between the proximal end 14a and the distal end 14b. The distal end 14b is adapted for use with needle cannula 12 wherein the needle cannula 12 has a length which is longer than the barrel length. The needle cannula 12 may have an end 22 opposed from the tip 13, which is secured within the hub 20. In one embodiment, the needle cannula 12 has an extended length of from about two inches to about five inches.

Figure 2:
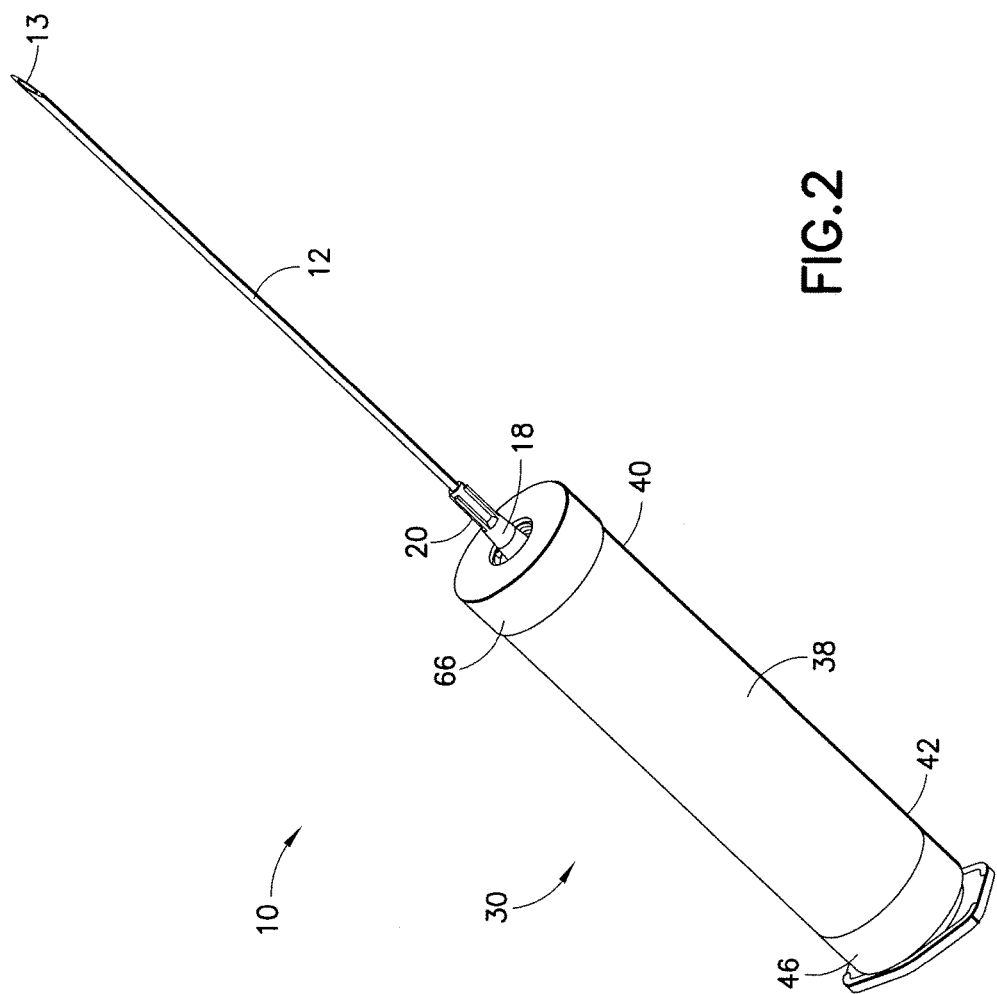
FIG. 2 is a perspective view of the syringe of FIG. 1 including the safety shield according to a first design of the invention mounted thereon and in a retracted position.
Figure 3:
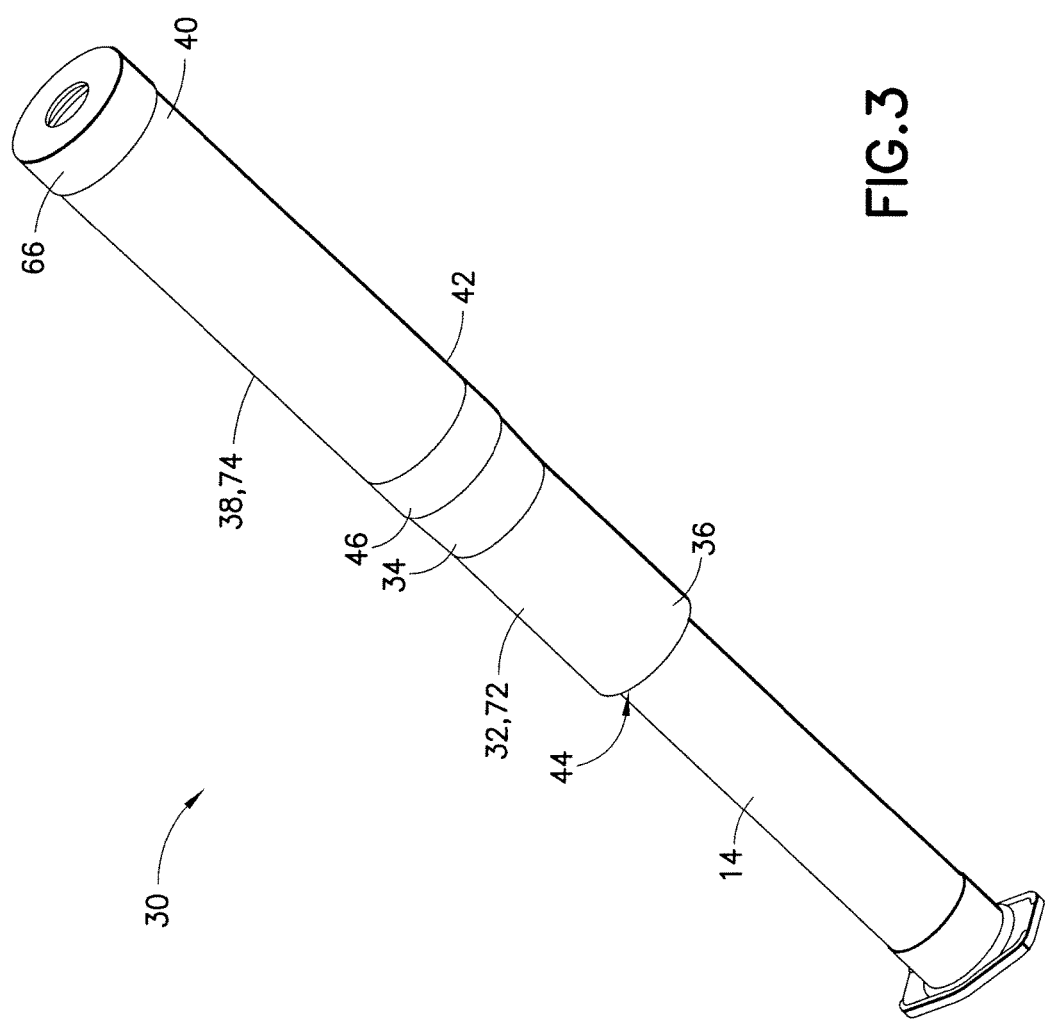
FIG. 3 is a perspective view of the syringe of FIG. 1 including the safety shield according to the first design of the invention mounted thereon in an extended position.
Figure 6:
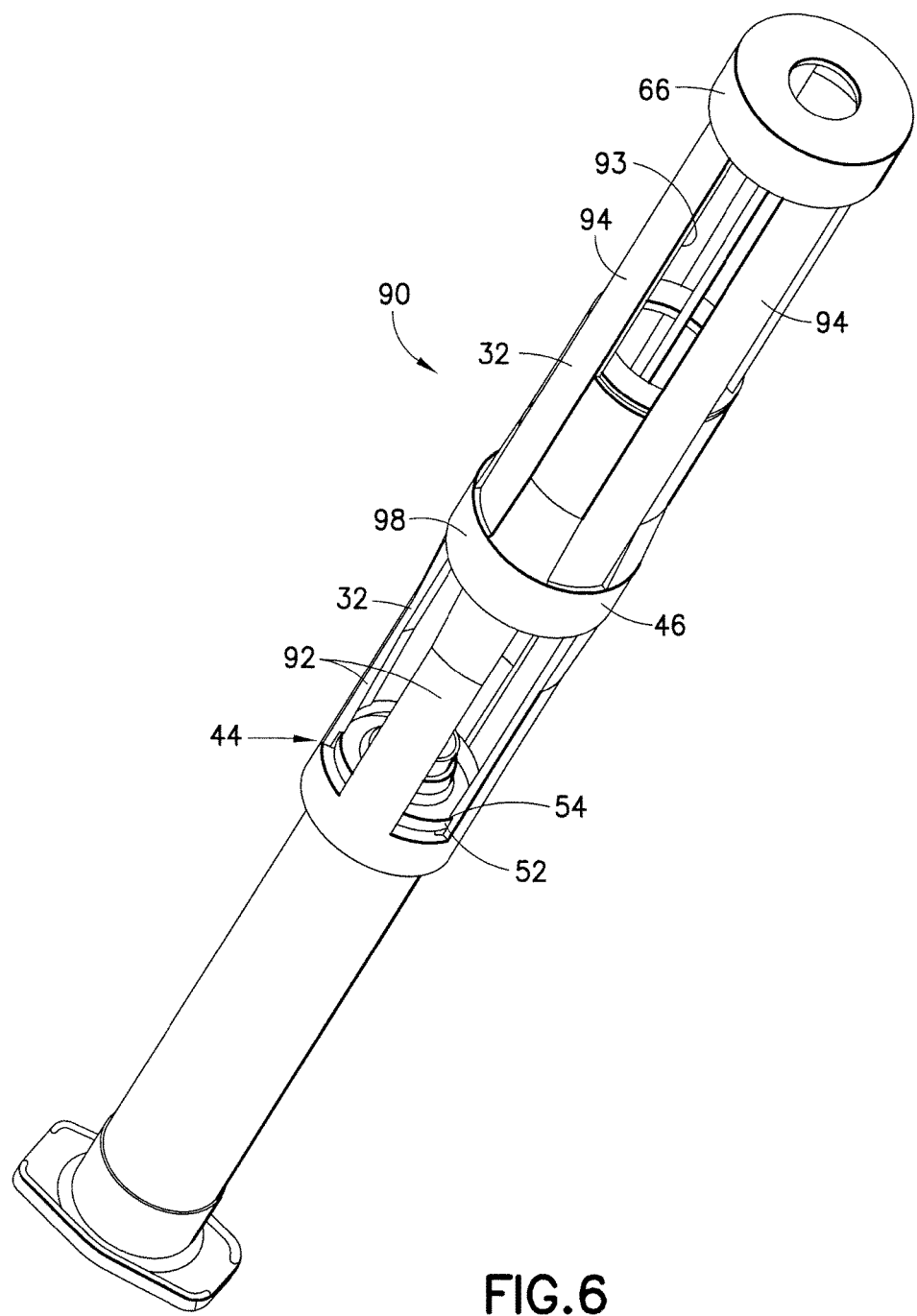
FIG. 6 is a perspective view of the syringe of FIG. 5A including the safety sheath according to the second design in the extended position.
Figure 7A:
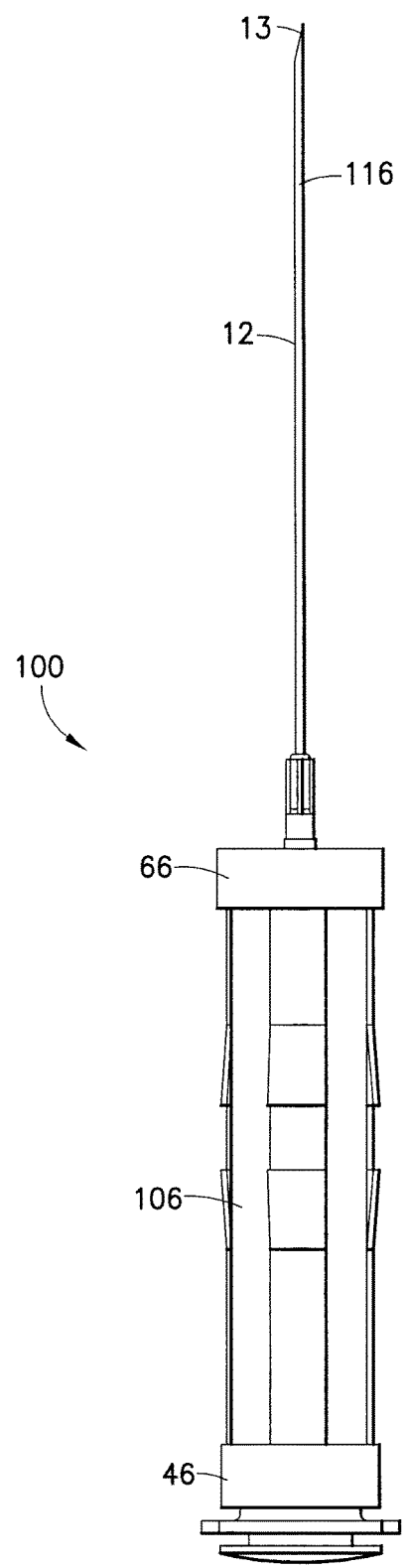
FIG. 7A is a side view of a syringe similarly configured to the syringe of FIG. 1 including a safety shield according to a third design of the invention in a retracted position.
Figure 8A:
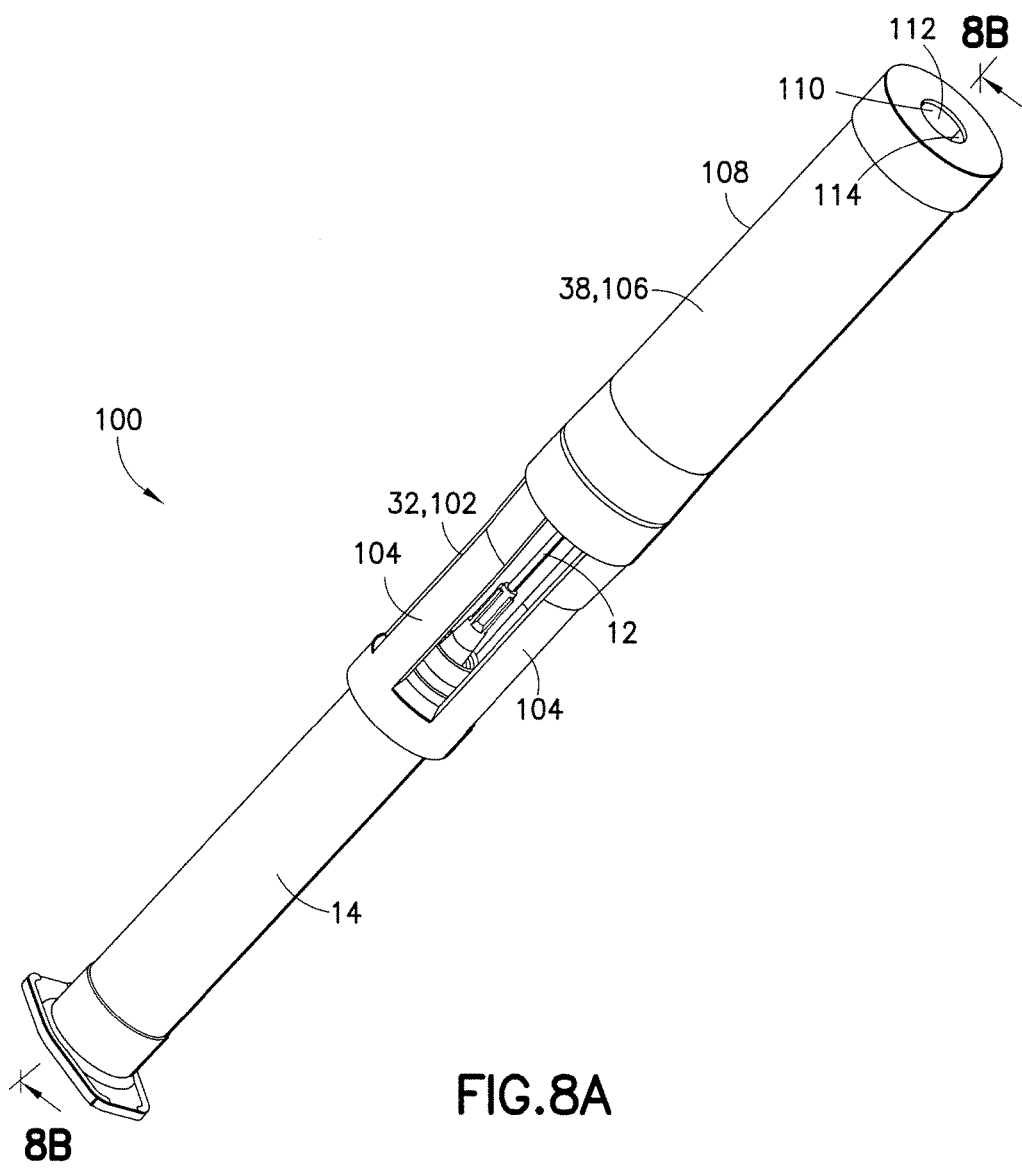
FIG. 8A is a perspective view of the syringe of FIG. 7 including the safety shield according to the third design of the invention in an extended position.
Figure 8B:
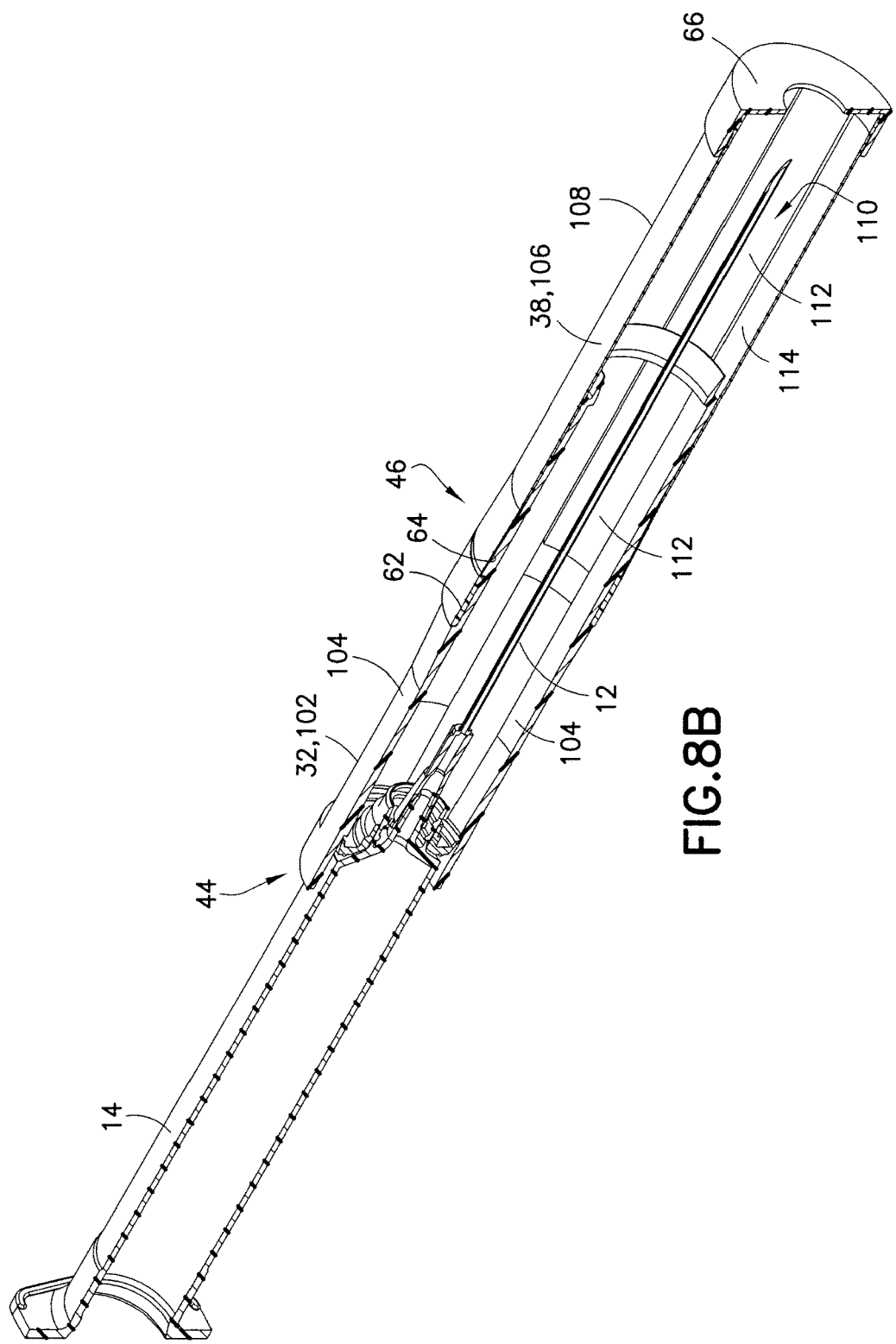
FIG. 8B is a cross-sectional view taken along line 8B-8B of FIG. 8A.

Reference is now made to FIGS. 2-3, which show the safety shield according to a first embodiment of the invention, generally indicated as 30. In one embodiment, the safety shield 30 is engaged with respect to an outer portion of the luer 18. In another embodiment, the safety shield 30 is engaged with respect to an outer portion of the syringe barrel 14. The safety shield 30 is adapted to transition from a retracted position or non-shielding position, shown in FIG. 2, to an extended position. In one embodiment, the tip 13 of the needle cannula 12 may be substantially exposed in the retracted position, and substantially safely shielded in the extended position. The safety shield 30 may include a first portion 32 which comprises inner portion 72 for enclosing at least a portion of a syringe barrel 14. The first portion 32 is adapted for telescoping movement from a retracted position to an extended position with respect to the syringe barrel 14 and includes a distal end 34 and a proximal end 36. The safety shield 30 further includes a second portion 38 comprising an outer portion 74 associated with the first portion 32 and adapted for movement from a retracted position to an extended position with respect to the first portion 32 and the syringe barrel 14. The second portion 38 includes a distal end 40 and a proximal end 42.

Figure 9:
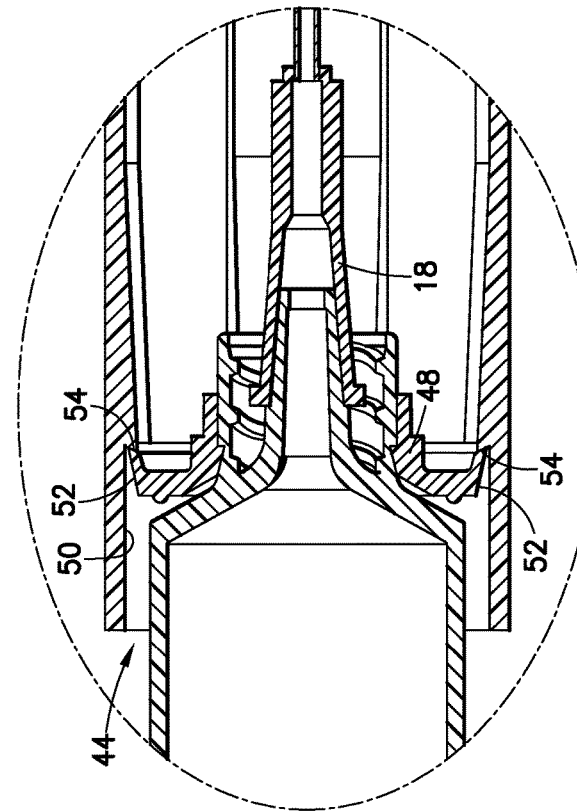
FIG. 9 is a close-up cross-sectional view of the first locking member, referenced as IX in FIG. 5B.

A first locking member 44, as illustrated in FIG. 9, is provided for restraining a portion of or locking the proximal end 36 of the first portion 32 with a portion of the luer 18 of the syringe 10 upon axial movement of the first portion/inner portion 32 with respect to the syringe barrel 14. In one embodiment, the locking member 44 restrains a portion of the first portion 32 with a portion of the luer 18 or syringe barrel upon transition of the first portion 32 from the retracted position to the extended position. A second locking member 46, shown in detail in FIG. 10, may be provided for restraining or locking the proximal end 42 of the second portion 38 with the distal end 34 of the first portion 32 upon axial movement of the second portion 38 from a retracted position to an extended position with respect to the first portion 32 and the syringe barrel 14. The distal end 40 of the second portion 38 may include a shield cap 66 which encompasses the needle cannula 12 and the needle tip 13 after use in a medical procedure. In one embodiment, the shield cap 66 extends beyond the needle cannula 12 and the needle tip 13 after use. This shield cap 66 prevents accidental needle sticks after the safety mechanism is locked in place.

After a medical procedure has been completed, the safety shield 30 is activated by moving the first and second portions 32, 38 together from the retracted to the extended position until the first locking member 44 restrains or locks the proximal end 36 of the first portion 32 to either the outer portion of the luer 18 or the outer portion of the syringe barrel 14. As illustrated in FIG. 9, the first locking member 44 comprises a locking collar 48 located on either the luer 18 or the barrel 14 of the syringe 10 for lockingly engaging an inner surface 50 of the proximal end 36 of the first portion 32 upon movement of the first portion 32 to the extended position. The locking collar 48 may include at least one detent 52 and the proximal end 36 of the inner surface 50 of the first portion 32 includes at least one barb 54 extending radially inward for engaging the at least one detent 52 to lock the first portion 32 in a shielding position. Preferably, the at least one barb 54 comprises a series of bilaterally opposing barbs which lock onto at least one circumferentially extending detent 52 on the locking collar 48.

Figure 10:
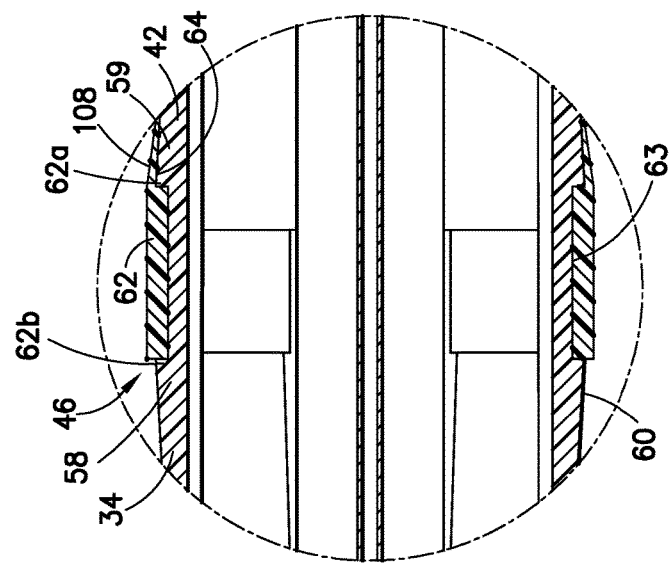
FIG. 10 is a close-up cross-sectional view of the second locking member, referenced as X in FIG. 5B.

The second locking member 46, as illustrated in FIG. 10, includes a first locking barb 58 and a second locking barb 59 positioned a predetermined distance from the first locking barb 58, the first and second locking barbs 58, 59 extending circumferentially about an outer surface 60 of the distal end 34 of the first portion 32 forming a circumferential channel 63. According to one embodiment, the first and second locking barbs 58, 59 can continuously extend about the outer surface 60 of the distal end 34 of the first portion 32. According to another embodiment, the first and second barbs 58, 59 can comprise a plurality of barbs axially-spaced about the circumference of the outer surface 60 of the distal end 34 of the first portion 32. The proximal end 42 of the second portion 38 includes a locking ledge 62 radially extending from an inner surface 64 of the continuous outer surface 108 of the second portion 38. The locking ledge 62 extends continuously about the inner circumference of the proximal end 42 of the second portion 38. The locking ledge 62 fits into the channel 63 upon extension of the second portion 38 with respect to the first portion 32 to lock the second portion 38 in the expanded position with respect to the first portion 32. The locking ledge 62 has a forward stop 62a and a rearward stop 62b. The first locking barb 58 cooperates with the locking ledge 62 at the rearward stop 62b to prevent the second portion 38 from retracting with respect to the first portion 32 upon expansion of the shield to the extended or shielding position. The second locking barb 59 cooperates with the forward stop 62a to prevent the second portion 38 from sliding further forward with respect to the first portion 32 upon expansion of the shield to the extended or shielding position resulting in locking of the first and second portions 32, 38 in place.

According to one embodiment, the distal end 40 of the second portion 38 can include a shield cap 66 for encompassing and/or extending beyond the end portion or tip 13 of the needle cannula 12 after use. Additionally, one or both first and second portions 32, 38 can include detents that prevent them from slipping during use. Upon the application of a sufficient axial force, the first and second portions 32, 38 can expand to the extended or shielding position.

As stated above, the safety shield 30 of the present invention is especially adapted for use with needle cannulas 12 having an extended length, however, the safety shield 30 of the present invention can be adapted for use with traditional sized needle cannulas 12 having a wide range of lengths. For use with extended length needles, the overall length of the safety shield 30 is preferably from one to two times the length of the syringe barrel 14. However, the shield can include an infinite number of extendable portions which can be expanded with respect to one another depending upon the length of the syringe barrel and/or the length of the needle cannula for which shielding is desired. For example, depending upon the length of the barrel, the shield can include three or more extendable portions which can be expanded to a length which is between two to three times the length of the syringe barrel. The length of the needle cannula 12 to be shielded by the safety shield 30 of the invention is typically dependent upon the size of the syringe barrel 14. According to the present invention, the needle shield 30 of the invention can shield a needle cannula 12 having a length of up to, and possibly exceeding, about five inches. As stated above, this extended length of the safety shield 30 is typically dependent upon the size of the syringe barrel 14 and is typically from approximately one to two times the actual length of the syringe barrel 14. For example, a three milliliter syringe barrel typically has a length of approximately two through two and a half inches. A safety shield 30 according to the present invention would have an extended length of approximately two and a half through five inches. A five milliliter syringe barrel typically has a length of approximately two and a half to two and three-fourths inches, and a ten milliliter syringe barrel typically has a length of approximately three through three and a half inches. The safety shield 30 of the present invention can be extended up to two times the barrel length for a particularly sized syringe.

The shield 30 can be formed from plastic, metal, or a combination of materials. In one embodiment, the shield 30 can be formed entirely from plastic material, i.e., thermosetting, thermoplastic, or a combination of known polymeric materials. Additionally, the shield 30 can be molded by a variety of plastic molding techniques including extrusion, injection molding, two-shot molding, compression molding, and transfer molding.

In operation, according to the first design of the safety shield, the first portion 32, which comprises inner portion 72, has a first diameter and the second portion 38, which comprises an outer portion 74, has a second diameter. The second diameter is greater than the first diameter and thus the outer portion 74 encloses at least a portion of the inner portion 72. The outer portion 74 is adapted for telescoping movement with respect to the inner portion 72. After a medical procedure has been completed, the safety shield 30 is activated, such as by a manual or passive activation, by moving the inner and outer portions 72, 74 together from the retracted to the extended position until the first locking member 44 locks a proximal end 36 of the inner portion 72 to either the outer portion of the luer 18 or the outer portion of the syringe barrel 14. The outer portion 74 continues extending until a second locking member 46 locks a proximal end 42 of the outer portion 74 to a distal end 34 of the inner portion 72. At this time, shield cap 66 located at a distal end 40 of the outer portion 74 surrounds the needle cannula 12 and the needle tip 13. The telescoping design of this first design enables the two-piece shield 30 to expand to nearly twice the length of the syringe barrel 14 so that needle cannulas 12 and their tips 13, which have an extended length, can be safely shielded. The clarity of the material used for the inner and outer portions 72, 74 must be of a degree to allow syringe markings to be clearly visible to the user. Additionally, the thickness of the inner and outer portions 72, 74 and the overall diameter of the shield 30 should be kept to a minimum to ensure proper handling of the syringe 10 and minimize the disposal volume of the activated device.

According to a second design of the invention, as shown in FIGS. 4A-4B, 5A-5B, and 6, the safety shield, generally indicated as 90, includes a first portion 32 having a first series of longitudinally extending, axially-spaced slats 92 arranged circumferentially defining a first diameter along the majority of the lengths of the first and second portions 32, 38, for enclosing at least a portion of the syringe barrel 14. The first portion 32 is adapted for telescoping movement with respect to the syringe barrel 14. The second portion 38 includes a second series of longitudinally extending axially-spaced slats 94 arranged between the first series of slats 92 when the shield is in the retracted position. The second series of slats 94 have a second diameter, which is substantially equal to the first diameter for enclosing at least a portion of the syringe barrel 14. The second portion 38 is adapted for telescoping movement with respect to the syringe barrel 14. In one embodiment, the first and second series of slats 92, 94 are adapted for interengaging contact with each other when the shield is in the retracted or non-shielding position. The first series of slats 92 and the second series of slats 94 are cut such that the slats match with one another, as shown at 93, to allow them to slide into each other similar to matching teeth. The number of slats in the first and second series 92, 94 can be as few as two per series or as many as the molding of the first and second portions 32, 38 will allow. This slatted design results in a single thickness of the shield 30 about the syringe barrel 14 maintaining good visibility of the graduated syringe markings and/or of the material contained within the syringe barrel 14.

An alignment member, generally indicated as 68 in FIG. 5B, may also be provided on the device to provide alignment of the first portion 32 within the second portion 38 during expansion of the safety shield 30. When the safety shield 30 is in the retracted position, this alignment member 68 prevents the first portion 32 from sliding back on the syringe barrel 14 and also prevents the second portion 38 from sliding back on the first portion 32.

According to this second design of the safety shield 90, the first locking member 44 is adapted for locking the proximal end 36 of the first portion 32 with respect to one of the luer 18 and/or the syringe barrel 14 upon axial movement of the first series of slats 92 of the first portion 32 from a retracted or non-shielding position to an extended or shielding position with respect to the syringe barrel 14. The second locking member 46 is adapted for locking the proximal end 36 of the second portion 38 with respect to the distal end 34 of the first portion 32 upon axial movement of the second series of slats 94 of the second portion 38 from a retracted or non-shielding position to an extended or shielding position with respect to the syringe barrel 14 wherein the shield cap 66 at distal end 40 of the second portion 38 encloses and/or extends beyond the needle cannula 12 and its tip 13 after use.

As shown in FIGS. 4A-4B, 5A-5B, and 6, the first portion 32 includes a first holding ring 96 for securing the first series of slats 92 thereto and the second portion 38 includes a second holding ring 98 for securing the second series of slats 94. The first and second holding rings 96, 98 are associated with one another to cause the first series of slats 92 to be held in interengaging contact with the second series of slats 94 such that axial movement of the second holding ring 98 with respect to the first holding ring 96 causes the first and second series of slats 92, 94 to become separated from one another to achieve expansion of the safety sheath 90. The safety sheath 90 further includes shield-to-shield locks 99 for holding the first portion and second portions 32, 38 in a non-shielding position during use of the syringe. Preferably these shield-to-shield locks 99 comprise interlocking side members positioned along the edges of the first and second series of slats 92, 94.

According to a third design of the invention, as shown in FIGS. 7A-7C and 8A-8B, the safety shield, generally indicated as 100, includes a first portion 32 which comprises an inner portion 102 having a first diameter. The inner portion 102 includes a first series of axially-spaced slats 104 arranged circumferentially defining the first diameter. The safety sheath 100 further includes a second portion 38 which comprises an outer portion 106 having a second diameter that is greater than the first diameter of the inner portion 102. The outer portion 106 has a continuous outer surface 108. The inner surface 110 of this outer portion 106 includes a second series of axially-spaced circumferential slats 112 extending inwardly from this inner surface 110 and connected by a series of axially-spaced circumferential connecting portions 114. These connecting portions 114 have a thickness that is complementary to the first series of slats 104. These connecting portions 114 are adapted for mating engagement with this first series of slats 104 when the sheath 100 is in a retracted or non-shielding position. Upon expansion of the shield 100, the second or outer portion 106 continuously surrounds the distal portion 116 of the needle cannula 12 and the shield cap 66 encompasses and/or extends beyond the needle tip 13. This design also maintains good visibility of the syringe barrel markings and contents therein due to the thickness of and cooperation between the first and second portions 32, 38 in the retracted or non-shielding position.

The present invention also discloses a method for enclosing an extended length needle cannula 12 used in a medical procedure. As discussed above, the extended length needle cannula 12 is from one to two times the length of the syringe barrel 14 and the safety shield 30 can be extended from one to two times the length of the syringe barrel 14 for safely enclosing this extended length needle cannula 12. The syringe to be shielded includes a syringe barrel 14 extending between a proximal end 14a and distal end 14b and defining a chamber therein. The syringe barrel 14 defines a barrel length between the proximal end 14a and the distal end 14b and is adapted at the distal end 14b thereof for use with a needle cannula 12 having a length longer than the barrel length. The method comprises providing a first portion 32 for enclosing at least a portion of a syringe barrel 14 and being adapted for telescoping movement from a retracted position surrounding at least a portion of the barrel 14 to an extended position with respect to the syringe barrel 14. The first portion 32 includes a distal end 34 and a proximal end 36. The method further comprises providing a second portion 38 associated with the first portion 32 and adapted for axial movement from a retracted to an extended position with respect to the first portion 32 and the syringe barrel 14. The second portion includes a distal end 40 and a proximal end 42. A first locking member 44 is provided for locking the proximal end 36 of the first portion 32 with respect to either an outer portion of the luer 18 or an outer portion of the syringe barrel 14. A second locking member 46 is provided for locking the proximal end 42 of the second portion 38 with respect to the distal end 34 of the first portion 32. The method further includes moving the first portion 32 in a forward direction from the retracted or non-shielding position to the extended or shielding position with respect to the syringe barrel 14 and moving the second portion 38 from the retracted or non-shielding position to the extended shielding position with respect to the first portion 32 to cause the second portion to surround the needle cannula 12 and its tip 13 after use.

According to the method, shielding the needle after use causes the first and second portions 32, 38 to move in unison from the retracted to the extended position until the first locking member 44 locks the proximal end 36 of the first portion 32 to either the luer 18 or the syringe barrel 14 and the second portion continues to be extended in the forward direction until a distal end 40 of the second portion 38 encompasses and/or extends beyond a distal end or tip 13 of the needle 12.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of this description. For example, it is to be understood that the present invention contemplates that, to the extent possible, one or more features of any embodiment can be combined with one or more features of any other embodiment.

The invention claimed is:

1. A safety shield adapted for use in connection with and attachable to a syringe barrel, the syringe barrel defining a barrel length between a proximal end and a distal end, the safety shield comprising:
    an inner portion for concentrically mounting about the syringe barrel and telescopingly moveable with respect to the syringe barrel from a retracted position to an extended position when the inner portion is concentrially engaged with the syringe barrel; and
    an outer portion concentrically mounted about the inner portion and mounted for telescoping movement with respect to the inner portion wherein the inner and outer portions are mounted for axial movement from the retracted position at least partially surrounding the syringe barrel to the extended position wherein at least a portion of the outer portion extends beyond a distal end of the inner portion and wherein the inner portion and the outer portion define an extended length which is approximately twice the barrel length of the syringe barrel.

2. The safety shield of claim 1, further comprising a first locking member for restraining the telescoping movement of the inner portion with respect to the syringe barrel.

3. The safety shield of claim 2, wherein the first locking member is provided on a proximal end of the inner portion for restraining the proximal end of the inner portion at a distal end of the syringe barrel.

4. The safety shield of claim 2, further comprising a second locking member for restraining the telescoping movement of the outer portion with respect to the inner portion.

5. The safety shield of claim 4, wherein the second locking member is provided on a proximal end of the outer portion for restraining the proximal end of the outer portion at a distal end of the inner portion.

6. The safety shield of claim 1, wherein the inner portion comprises a first series of longitudinally extending, axially-spaced slats arranged circumferentially defining a first diameter, and being adapted for axial movement from the retracted position to the extended position, and the outer portion comprises a second series of longitudinally extending axially-spaced slats arranged between the first series of slats in the retracted position, the second series of slats being adapted for axial movement from the retracted position to the extended position with respect to the first series of slats.

7. The safety shield of claim 1, wherein the inner portion comprises a first diameter defined by a first series of axially-spaced circumferentially arranged slats, and the outer portion comprises a second diameter which is greater than the first diameter for enclosing at least a portion of the inner portion, wherein the outer portion has a continuous outer surface and an inner surface comprising a second series of axially-spaced circumferentially arranged slats connected by a series of axially-spaced connecting portions and wherein the axially-spaced connecting portions are adapted for mating engagement with the first series of axially-spaced slats when the inner and outer portions are in the retracted position.

8. The safety shield of claim 1, wherein the lengths of the first portion and the second portion are approximately equal.

* * * * *

UNITED STATES PATENT AND TRADEMARK OFFICE
CERTIFICATE OF CORRECTION

PATENT NO. : 10,406,296 B2
APPLICATION NO. : 15/667158
DATED : September 10, 2019
INVENTOR(S) : Michael Quinn et al.

Page 1 of 1

It is certified that error appears in the above-identified patent and that said Letters Patent is hereby corrected as shown below:

In the Claims

Column 13, Line 53, Claim 1, delete "concentrially" and insert -- concentrically --

Signed and Sealed this
Nineteenth Day of November, 2019

Andrei Iancu
*Director of the United States Patent and Trademark Office*